United States Patent
Cochran et al.

[11] Patent Number: 5,973,171
[45] Date of Patent: Oct. 26, 1999

[54] PROPYLENE OXIDE PRODUCTION

[75] Inventors: Robert N. Cochran; John C. Jubin, Jr., both of West Chester; Mark A. Liepa, Exton; Robert Nedwick, Broomall; Rangasamy Pitchai, West Chester, all of Pa.; W. Wayne Wentzheimer, Grand Rapids, Mich.

[73] Assignee: ARCO Chemical Technology, LP, Greenville, Del.

[21] Appl. No.: 09/167,329

[22] Filed: Oct. 7, 1998

[51] Int. Cl.[6] .................................................. C07D 301/06
[52] U.S. Cl. ........................................... 549/533; 549/532
[58] Field of Search ........................................ 549/532, 533

[56] References Cited

U.S. PATENT DOCUMENTS

| | | | |
|---|---|---|---|
| 4,410,501 | 10/1983 | Taramasso et al. | 423/326 |
| 4,990,632 | 2/1991 | Ramachandran et al. | 549/523 |
| 5,008,412 | 4/1991 | Ramachandran et al. | 549/523 |
| 5,466,836 | 11/1995 | Jubin | 549/531 |
| 5,599,956 | 2/1997 | Pujado et al. | 549/531 |

FOREIGN PATENT DOCUMENTS

| | | |
|---|---|---|
| 0850936 | 7/1998 | European Pat. Off. . |
| 4-352771 | 12/1992 | Japan . |

*Primary Examiner*—Ba K. Trinh
*Attorney, Agent, or Firm*—William C. Long

[57] ABSTRACT

An integrated process is provided for the production of propylene oxide from propane wherein propane is dehydrogenated to propylene and hydrogen and the resulting propylene, propane, and hydrogen mixture together with added oxygen is reacted over a palladium on titanium silicilite catalyst to form propylene oxide, the molar ratio of oxygen to hydrogen in the reaction feed being at least about 2/1.

5 Claims, 1 Drawing Sheet

PROPYLENE OXIDE PRODUCTION

BACKGROUND OF THE INVENTION

1. Field of the Invention

The present invention relates to the production of propylene oxide by a process wherein propane is dehydrogenated and the product mixture comprised of propylene, propane and hydrogen from the dehydrogenation, together with added oxygen, is reacted to form propylene oxide.

2. Description of the Prior Art

Integrated processes have been proposed wherein propane is dehydrogenated to form propylene with the propylene being epoxidized, using a hydroperoxide or hydrogen peroxide, to form propylene oxide. See, for example, U.S. Pat. No. 5,599,956. Such prior procedures have required the costly separation of propylene from hydrogen in the dehydrogenation product prior to the epoxidation of the propylene to propylene oxide.

In addition, methods have been proposed such as suggested in U.S. Pat. Nos. 4,990,632 and 5,008,412 wherein propane is dehydrogenated and the resultant propylene is oxidized to propylene oxide using a catalyst such as silver oxide; oxygen is eliminated by oxidation from the recycle stream.

Further, in EP 0850936 a process is described wherein propane is dehydrogenated, oxygen is added to the dehydrogenation product and the resulting mixture is epoxidized over a gold catalyst with oxygen being eliminated from the recycle stream.

The instant invention represents a significant improvement over prior procedures in that the mixture of propylene, propane, and hydrogen from the propane dehydrogenation is used, without separation of the components, to form propylene oxide over a Pd/TS-1 catalyst with recycle of oxygen to the epoxidation.

SUMMARY OF THE INVENTION

In accordance with the invention, propane is dehydrogenated to a dehydrogenation product comprised of propylene, propane, and hydrogen. The mixture of propylene, propane, and hydrogen together with added oxygen and such additional hydrogen as may be needed is contacted with an epoxidation catalyst such as a Pd/TS-1 catalyst at epoxidation conditions to form propylene oxide.

BRIEF DESCRIPTION OF THE DRAWING

The accompanying drawing illustrates schematically an embodiment of the invention.

DETAILED DESCRIPTION

Figure 1:
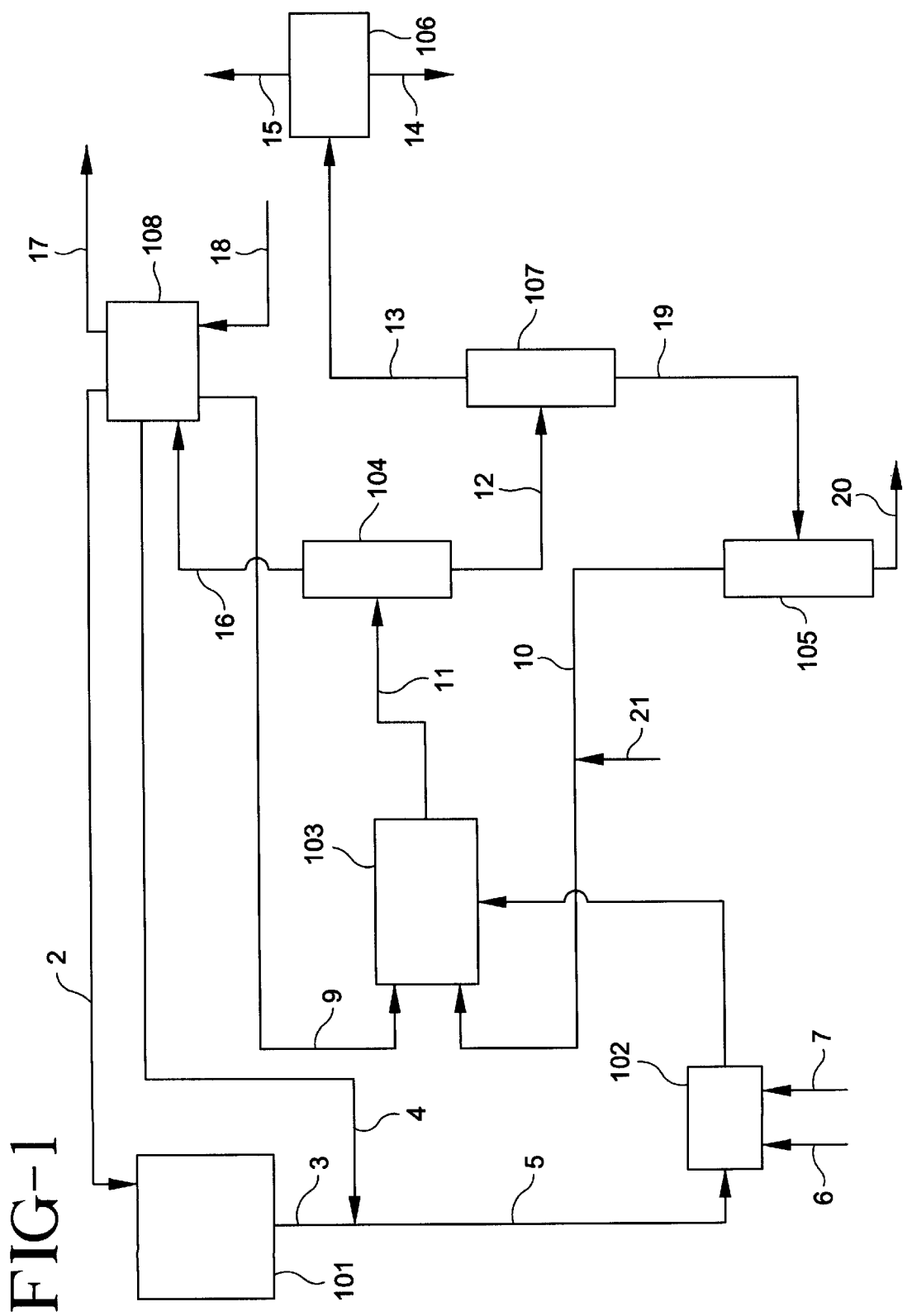

Referring to the drawing, net feed propane is introduced into dehydrogenation zone 101 via line 1 along with recycle propane which is introduced via line 2. In zone 101 the propane is dehydrogenated to form propylene and hydrogen. Commercially practiced technology for this dehydrogenation step is represented for example, by the UOP OLEFLEX process or the CATOFIN process of United Catalysts/Lummus Crest.

The dehydrogenation reaction product mixture comprised of unreacted propane, propylene and hydrogen is removed from dehydrogenation zone 101 via line 3, combined with recycle vapor via line 4 and the mixture passed via line 5 to oxygen mixing station 102 wherein the mixture is mixed with oxygen fed via line 6 and hydrogen fed via line 7. The resulting vapor feed passes via line 8 to epoxidizer 103.

Also fed to epoxidizer 103 via line 9 is a liquid $C_3$'s recycle stream. It is preferred to carry out the epoxidation using a solvent such as methanol and this is introduced via line 10 to the epoxidizer.

In zone 103 propylene, hydrogen and oxygen are contacted at reaction conditions with an effective catalyst to produce propylene oxide. The epoxidation reaction is, itself, a known reaction as shown, for example, in Japanese Kokai No. 4-352771 where the reaction of propylene, hydrogen and oxygen over a catalyst comprised of a Group VIII metal and a crystalline titanosilicate to form propylene oxide is described.

It is important that a substantial molar excess of oxygen relative to hydrogen be fed to the epoxidation in order to achieve a reasonable reaction rate and selectivity to propylene oxide. Generally the $O_2/H_2$ mol ratio fed to zone 103 should be 2/1 or higher, eg. 2/1–5/1.

The reaction mixture from epoxidation zone 103 passes via line 11 to separation zone 104. In zone 104, the readily condensible propylene oxide and solvent are separated from the lighter materials comprised of propane, propylene, oxygen and hydrogen. The propylene oxide and solvent mixture is removed from zone 104 and passes via line 12 to separation zone 107. This mixture is distilled in zone 107 and an overhead product propylene oxide stream is removed via line 13 and transferred to zone 106 wherein by known procedures purified propylene oxide is recovered via line 14 and lighter fuel value materials are recovered via line 15.

The light materials from separation zone 104 pass via line 16 to $C_3$ recovery zone 108 where lighter materials are separated as by distillation from the $C_3$ components. Lights which have a significant fuel value are recovered via line 17 while the propane/propylene and excess $O_2$ and $H_2$ vapor components are recycled via lines 2 and 4. Methane is introduced via line 18 to prevent flammability of the fuel mixture.

Most of the $C_3$ stream is recycled to epoxidation as above described. A minor amount, eg. about 4% of the stream is recycled via line 2 to dehydrogenation zone 101 as above indicated.

A liquid propylene and propane stream is recycled via line 9 to epoxidation zone 103.

From separation zone 107, a bottoms stream comprised of solvent passes via line 19 to separation zone 105 from which solvent is removed via line 10 and recycled to epoxidation zone 103. A stream comprised of water and fuel value organics is removed via line 20. Make up solvent is introduced through line 21 into the system.

It can be seen that the process of the present invention is distinctly advantageous in that costly separation of the components of the dehydrogenation reaction mixture as previously thought necessary is avoided. Propylene oxide is produced in high efficiency and with substantial economics of operation.

Both the CATOFIN and OLEFLEX processes are described in Kirk-Othmer "Encyclopedia of Chemical Technology", Fourth Edition, Vol 20, P. 259–260 (1996). As described therein, the CATOFIN process uses a relatively inexpensive and durable chromium oxide-alumina as catalyst. This catalyst can be easily and rapidly regenerated under severe conditions without loss in activity. To improve propylene selectivity and to increase the propane conversion, this technology uses a vacuum. Dehydrogenation is carried out in the gas phase over fixed beds. Because the catalyst cokes up rapidly, five reactors are typically used. Two are on-stream while two are being regenerated and one is being purged. The reactors are cycled between the reaction and the reheat/regeneration modes, and the thermal inertia of the catalyst controls the cycle time, which is typically less than 10 minutes.

The OLEFLEX process uses multiple side-by-side radial flow moving-bed reactors connected in series. The heat of reaction is supplied by preheated feed and interstage heaters. The gas-phase reaction is carried out over a catalyst, platinum supported over alumina, under very near isothermal conditions. Other known dehydrogenation procedures can be used.

The dehydrogenation is equilibrium limited and per pass yield of propylene is quite low. Accordingly the dehydrogenation effluent contains substantial amounts of unreacted propane which, in preferred practice serves as a ballast gas in subsequent steps. Generally, about 1 mol of hydrogen is contained in the dehydrogenation effluent per mol of propylene.

Epoxidation in zone 103 is carried out at reaction temperatures of 50 to 100° C., and preferably 50 to 70° C. Pure oxygen can be used as one of the starting materials for the reaction.

The amounts of the several starting materials contained in the gas can vary. Generally 10 to 50 vol % propylene, 5 to 20 vol % hydrogen, and 10 to 50 vol % oxygen are suitable on a ballast gas free basis with the $O_2/H_2$ ratio being at least 2/1. From the standpoint of safety, it is desirable for the contained amount of the several starting materials to be outside of the explosive range. Preferably propane is used as a ballast gas although other gases such as nitrogen, methane, and the like are useful.

System pressures in the range 50 to 500 psia are suitable.

In the epoxidation, a catalyst comprising a Group VIII metal and a crystalline titanosilicate is used. The titanosilicate referred to here is obtained by substitution of a portion of the silicon which forms the crystal lattice of "Silicalite" (crystalline $SiO_2$ having a zeolite structure, developed by E. M. Flanigen (Nature, 271, 512 (1978)) mainly with titanium. The titanosilicate may be synthesized by any desired method; an example of synthesis is disclosed in Japanese Laid-Open Patent application 56-96720. The amount of titanium contained in said titanosilicate may be defined as the silica/titania ratio (molar), and said silica/titania ratio should be 5 to 200. If the titanium content is too low the activity of the catalyst will be insufficient. Components of the titanosilicate are not restricted to titanium; one or more additional elements such as boron, aluminum, phosphorus, vanadium, chromium, manganese, iron, gallium, or zirconium may also be contained therein.

The prepared titanosilicate may be used without modification, or molded. It is common to use a binder when preparing a molded form; there are no restrictions regarding the type of binder, which may be silica, alumina, or the like. In the catalyst any of the Group VIII metals may be used. Typical examples include palladium, platinum, iridium, rhodium, ruthenium, and the like; palladium is particularly desirable. The Group VIII metal may be supported on the crystalline titanosilicate, or first supported on silica, alumina, activated carbon or the like and then physically mixed with the titanosilicate. There are no particular restrictions regarding the starting material to be supported when supporting a Group VIII metal; examples include palladium (II) chloride, tetraaminepalladium(II) chloride, and palladium(II) acetate when palladium is used. There are no restrictions regarding the method for supporting these metals on the titanosilicate; an immersion method or the like may be used.

The Group VIII metal content, with respect to the titanosilicate, should be 0.1 to 10 wt % as metal atoms. Efficacy will be diminished if the content falls below 0.1 wt %, and amounts in excess of 10 wt % are undesirable from an economic standpoint. When the Group VIII metal is supported on titanosilicate using an immersion process, the catalyst may be baked and/or reduced prior to use. Baking may be performed under a stream of an inert gas or an oxygen-containing gas. There are no particular restrictions regarding baking temperature and duration, but baking at 100 to 700° C. for 30 minutes to 24 hours is satisfactory. When reduction is performed, there are no particular restrictions regarding the reducing agent or the reduction temperature and duration as long as the metal component is reduced; reduction at room temperature to 500° C. for 30 minutes to 24 hours using hydrogen as a reducing agent is satisfactory.

The prepared catalyst may be used without modification or by adding a diluent such as silica or alumina prior to use in reactions. The prepared Group VIII metal-supporting zeolite catalyst may be reduced under a hydrogen-containing gas flow prior to use in reactions.

If necessary, a solvent such as water, alcohols having a carbon number of 6 or less, ethers, esters, ketones, glycols, carboxylic acids and the like may be used. Methanol is especially preferred.

The reaction process may be of a continuous flow, semi-batch, or batch type; a continuous flow process is preferable from a productivity standpoint.

The following example illustrates an embodiment of the invention with reference to the attached drawing. Table 1 shows the flow rates of the various components for the indicated process streams.

Referring to the drawing, net feed propane is introduced into dehydrogenation zone 101 via line 1 along with recycle propane which is introduced via line 2. In zone 101 the propane is dehydrogenated to form propylene and hydrogen. The dehydrogenation is carried out by the known CATOFIN process of United Catalysts/Lummus Crest. The catalyst is chromic oxide on alumina, the dehydrogenation temperature is 525–677° C. and pressure is 0.1–0.7 atmospheres absolute. LHSV is less than 1

In reactor 1 conversion of propane is about 60% and the selectivity to propylene is about 85%.

The dehydrogenation reaction product mixture comprised of unreacted propane, propylene and hydrogen is removed from dehydrogenation zone 101 via line 3, combined with a recycle oxygen/hydrogen/propane/propylene vapor stream via line 4 and the mixture passed via line 5 to oxygen mixing station 102 wherein it is mixed with oxygen fed via line 6 and hydrogen fed via line 7. The resulting vapor feed is passed via line 8 to epoxidizer 103.

Also fed to epoxidizer 103 via line 9 is a liquid propylene recycle stream. It is preferred to carry out the epoxidation using a solvent such as methanol and this is introduced via line 10 to the epoxidizer.

In zone 103 propylene, hydrogen and oxygen are contacted at reaction conditions with an effective catalyst to produce propylene oxide. The epoxidation reaction is, itself, a known reaction as shown, for example, in Japanese Kokai No. 4-352771 where the reaction of propylene, hydrogen and oxygen over a catalyst comprised of a Group VIII metal and a crystalline titanosilicate to form propylene oxide is described.

Generally speaking, slurry techniques wherein the solid catalyst is slurried in an appropriate liquid or fixed bed epoxidation procedures can be employed. In the embodiment herein described, the catalyst is a palladium on titanium silicalite as described in Japanese Kokai No. 4-352771. A fixed bed reactor of the type described in U.S. Pat. No. 5,466,836 is employed with downflow of the reactants.

Epoxidation temperature is about 65° C. (generally 50–95° C. is suitable) and pressure is about 230 psia (200–300 psia is a useful range). About 22% propylene conversion with 70% molar selectivity to propylene oxide is achieved.

The reaction mixture from epoxidation zone 103 passes via line 11 to separation zone 104. In zone 104, the readily condensible propylene oxide and solvent are separated from the lighter materials comprised of propane, propylene, oxygen and hydrogen. The propylene oxide and solvent are removed from zone 104 and passed via line 12 to separation zone 107. The mixture is distilled in zone 107 and an overhead product propylene oxide stream is removed via line 13 and transferred to zone 106 wherein by known procedures purified propylene oxide is recovered via line 14.

The light materials from separation zone 104 pass via line 16 to $C_3$ recovery zone 108 where a purge gas containing the light materials is separated as by distillation from the $C_3$ components. Lights which have a significant fuel value are recovered via line 17 while the propane/propylene components and unreacted oxygen and hydrogen are recycled. Methane is introduced via line 18 to control flammability.

The $C_3$ components are resolved by known procedures (not shown) with a propane stream being recycled via line 2 to dehydrogenation 101 as above indicated.

From separation zone 107, a bottoms stream comprised of solvent passes via line 19 to separation zone 105 from which solvent is removed via line 10 and recycled to epoxidation zone 103. A stream comprised of water and fuel value organics is removed via line 20. Make up solvent is introduced through line 21.

For purposes of simplicity, the attached drawing illustrates various operations as taking place in a single zone. Actually, however, in many of the steps a plurality of operations such as various separations are suitably employed as will be apparent to those skilled in the art.

The following Table 1 shows the appropriate flow rates of the various components of the process streams.

TABLE 1

| Component, lbs/hr | 1 | 2 | 3 | 4 | 6 | 7 | 5 |
|---|---|---|---|---|---|---|---|
| Propylene |  | 10332 | 92329 | 229594 |  |  | 321923 |
| Propane | 75291 | 92985 | 67215 | 2066342 |  |  | 2133556 |
| Propylene Oxide |  |  |  |  |  |  |  |
| Oxygen |  |  |  | 116327 | 73251 |  | 116327 |
| Hydrogen |  |  | 3905 | 9694 |  | 3371 | 13599 |
| Water |  |  |  |  |  |  |  |
| Methanol |  |  |  |  |  |  |  |
| Fuel |  |  | 15159 |  |  |  |  |

| Component, lbs/hr. | 9 | 10 | 11 | 13 | 14 | 15 | 20 | 21 |
|---|---|---|---|---|---|---|---|---|
| Propylene | 57398 |  | 297324 |  |  |  |  |  |
| Propane | 516585 |  | 2675912 |  |  |  |  |  |
| Propylene Oxide |  |  | 79264 | 79264 | 75301 | 3963 |  |  |
| Oxygen | 29082 |  | 153062 |  |  |  |  |  |
| Hydrogen | 2423 |  | 12755 |  |  |  |  |  |
| Water |  | 10000 | 59199 |  |  |  | 49199 |  |
| Hydrogen Peroxide |  |  |  |  |  |  |  |  |
| Methanol |  | 2190727 | 2195117 | 7580 |  |  | 4390 | 4390 |
| Fuel |  |  | 15159 |  |  | 7580 |  |  |

| Component lbs/hr | 12 | 19 | 16 | 17 | 18 |
|---|---|---|---|---|---|
| Propylene |  |  | 297324 |  |  |
| Propane |  |  | 2675912 |  |  |
| Propylene Oxide | 79264 |  |  |  |  |
| Oxygen |  |  | 153062 | 7653 |  |
| Hydrogen |  |  | 12755 | 638 |  |
| Water | 59199 | 59199 |  |  |  |
| Hydrogen Peroxide |  |  |  |  |  |
| Methanol | 2195117 | 7580 |  |  |  |
| Fuel | 7580 |  | 7580 | 56123 | 48543 |

We claim:

1. The process for preparing propylene oxide which comprises:

a) dehydrogenating propane to a dehydrogenation product mixture comprised of propylene, propane, and hydrogen, and
b) reacting the said mixture of propylene, propane, and hydrogen together with added oxygen over a palladium on titanosilicate catalyst in a reaction step at reaction conditions effective to form propylene oxide, the molar ratio of oxygen to hydrogen in the reaction feed being at least 2/1.

2. The process of claim 1 wherein the molar ratio of oxygen to hydrogen in the reaction feed is in the range 2/1–5/1.

3. The process of claim 1 wherein unreacted oxygen is recycled to the said reaction step.

4. The process of claim 1 wherein the reaction conditions involve use of a solvent.

5. The process of claim 4 wherein the solvent is methanol.

* * * * *